United States Patent [19]

Sacks et al.

[11] Patent Number: 5,141,532
[45] Date of Patent: Aug. 25, 1992

[54] THERMAL MODULATION INLET FOR GAS CHROMATOGRAPHY SYSTEM

[75] Inventors: Richard D. Sacks; Christine L. Rankin, both of Ann Arbor, Mich.

[73] Assignee: The Regents of the University of Michigan, Ann Arbor, Mich.

[21] Appl. No.: 710,703

[22] Filed: Jun. 5, 1991

Related U.S. Application Data

[63] Continuation-in-part of Ser. No. 590,174, Sep. 28, 1990, Pat. No. 5,096,471.

[51] Int. Cl.⁵ .............................. B01D 15/08
[52] U.S. Cl. ........................... 55/67; 55/197; 55/208; 55/267; 55/386
[58] Field of Search ............... 55/67, 197, 208, 267, 55/269, 386, 18-21

[56] References Cited

U.S. PATENT DOCUMENTS

| | | | |
|---|---|---|---|
| 3,111,835 | 11/1963 | Jenkins | 73/23 |
| 3,220,164 | 11/1965 | Golay | 73/23.42 X |
| 3,550,428 | 12/1970 | Mator et al. | 73/23.36 |
| 3,948,602 | 4/1976 | Solomon | 55/386 X |
| 4,035,168 | 7/1977 | Jennings | 55/386 X |
| 4,477,266 | 10/1984 | Yang et al. | 55/67 |
| 4,805,441 | 2/1989 | Sides et al. | 55/67 X |
| 4,863,871 | 9/1989 | Munari et al. | 55/386 X |
| 4,923,486 | 5/1990 | Rubey | 55/386 X |
| 5,028,243 | 7/1991 | Rubey | 55/386 X |

OTHER PUBLICATIONS

"Sample Enrichment in High Speed Narrow Bore Capillary Gas Chromatography", van Es et al., *J. High Resolution Chromatography & Chromatography Communications*, vol. 11, Dec. 1988, 852-857.

"Rapid Evaporation of Condensed Gas Chromatographic Franctions", Hopkins et al., *J. of Chromatography*, 158, (1978), 465-469.

B. A. Ewels and R. D. Sacks, "Electrically Heated Cold Trap Inlet System for High-Speed Gas Chromatography", *Anal. Chemistry*, Dec. 1985, 57, 2774-2779, No. 14.

Lanning, Sacks, Mouradian, Levine, Foulke, "Electrically Heated Cold Trap Inlet System for Computer-Controlled Controlled High-Speed Gas Chromatography", *Anal. Chem.*, 1988, 60, 1994-1996.

S. Levine, R. Sacks, Jul. 1, 1986-Jun. 30, 1986, "Fast-GC for Industrial Hygiene Monitoring/Analysis", Grant No. 86-863-J1.

*Primary Examiner*—Robert Spitzer
*Attorney, Agent, or Firm*—Harness, Dickey & Pierce

[57] ABSTRACT

A gas chromatography system which incorporates a simplified sample injection system in which replaces conventional mechanical injection systems with one based strictly upon thermal trapping of a continuously supplied carrier gas and sample stream. The carrier gas and sample stream pass continuously through the device which incorporates a thermal focusing chamber which communicates with the inlet end of a gas chromatography separation column. By causing the focusing chamber temperature of a sample tube passing through the focusing chamber to be dropped, incoming components comprising the sample stream are condensed and trapped. Injection into the column occurs rapidly heating the sample in the thermal focusing chamber causing a narrow sample plug to be introduced into the column. Various embodiments of this invention are intended for operation for evaluating carrier gas and sample stream provided at a above atmospheric pressure, or which are drawn through the system by vacuum source at the outlet end of the column. In addition, vacuum backflushing features are also described.

9 Claims, 1 Drawing Sheet

THERMAL MODULATION INLET FOR GAS CHROMATOGRAPHY SYSTEM

CROSS REFERENCE TO RELATED APPLICATION

This application is a continuation-in-part of co-pending U.S. patent application Ser. No. 590,174, filed on Sep. 28, 1990, now U.S. Pat. No. 5,096,471, entitled "Gas Chromatography System and Method".

BACKGROUND AND SUMMARY OF THE INVENTION

This invention relates to an apparatus for gas chromatography, and particularly, to an inlet system for such an apparatus.

Gas chromatography is a widely employed technique for the separation and analysis of complex mixtures of volatile organic and inorganic compounds. The analyte mixture is separated into its components by eluding them from a column having a sorbent by means of moving gas.

Gas chromatography procedures can be classified into two major divisions; gas-liquid chromatography, and gas-solid chromatography. Gas-liquid chromatography is presently the most widely employed type and incorporates a nonvolatile liquid sorbent coated as a thin layer on an inner support structure, generally the inside surface of a capillary tube. The moving gas phase, called the carrier gas, flows through the chromatography column. The analyte partitions itself between the moving gas phase and the sorbent, and moves through the column at a rate dependent upon the partition coefficient or solubility of the analyte components. The analyte is introduced at the entrance end of the column within the moving carrier gas stream. The components making up the analyte become separated along the column and escape from the exit end of the column at intervals and in concentrations characteristic of the properties of the analyte components. A detector, for example, a thermal conductivity detector or a flame ionization detector (FID) at the exit end of the column responds to the presence of analyte components. Upon combustion of the eluded material at the FID, charged species are formed in the flame. The flame behavior is monitored through a biased ion detector which, along with associated electronics, produces a chromatogram which is a time versus magnitude trace of the detector output. The trace for a complex mixture includes numerous peaks of varying intensity. Since individual constituents of the analyte produces peaks at characteristic times and whose magnitude is a function of their concentration, much information is gained through an evaluation of the chromatogram.

Gas chromatography systems of the type described above are in widespread use today. Although present systems provide excellent performance and utility, this invention seeks to provide improvements in gas chromatography systems; principally through simplifying the systems and increasing their speed and operational flexibility. Conventional gas chromatography system employs a mechanical system for the injection of analyte. For example, mechanical valves, or needles and septum type injection techniques are presently used. Such mechanical techniques contribute to system complexity, both in terms of their presence in the system and their control requirements. Conventional gas chromatography apparatuses are also unsatisfactory for high-speed analysis, since the column injection bandwidths are excessively large.

In accordance with the present invention, a gas chromatography system is provided in which no mechanical barriers are used to control the flow of analyte into the system. Instead, a thermal focusing chamber is provided at sub-ambient temperatures which is used as the exclusive means for controlling flow of analyte components into the separation column. The analyte stream continually flows into the thermal focusing chamber. Its introduction into the separation column, however, is controlled by the temperature of the sample tube in the thermal focusing chamber.

The injection system of this invention allows the high speed, repetitive sampling of a continuously flowing sample stream. With this invention, relatively simple mixtures can be separated faster than with current commercial apparatuses. Since the system has no moving parts, it is very rugged, and can operate for many cycles with minimal maintenance.

The flexibility of the inlet system according to this invention is demonstrated by the variety of optional modes it supports. In addition to high-pressure inlet operation with the column outlet at atmospheric pressure, the system is also capable of ambient and sub-ambient pressure inlet with vacuum outlet, and with vacuum backflush features. All of these modes of operation can be computer controlled.

This invention provides potential applications for numerous gas chromatography procedures, including those practiced by process engineers and chemists, industrial hygiene workers, and others interested in the continuous monitoring of volatile organic mixtures.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE INVENTION

Figure 1:
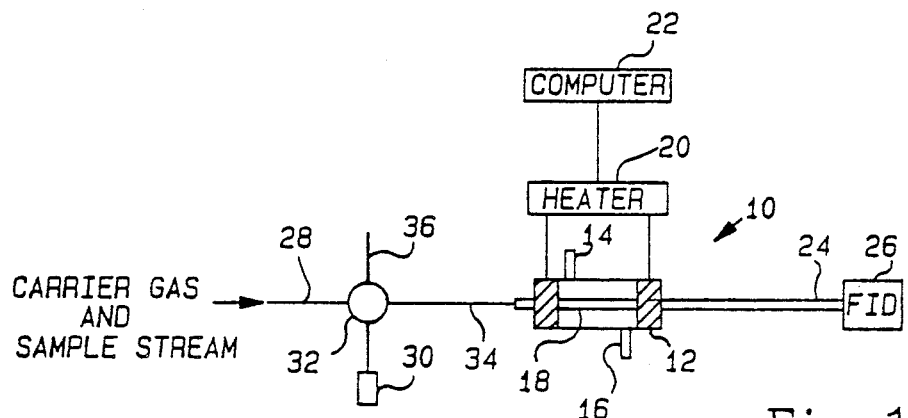
FIG. 1 is a schematic view of a gas chromatography system in accordance with a first embodiment of this invention for use with a sample introduced into the system at a positive pressure and the column outlet vented to atmosphere.

A gas chromatography system in accordance with a first embodiment of this invention is shown in FIG. 1 and is designated there by reference number 10. Gas chromatography system 10 includes a thermal focusing chamber or trap 12 having inlets and outlets 14 and 16, respectively, for conducting the flow of a cryogenic gas such as nitrogen. A short length of metal capillary sample tube 18 passes through chamber 12 and conducts the analyte through the chamber. Heater circuit 20 is connected to metal sample tube 18 via a pair of conductive blocks (or by direct soldering) and provides a short duration, high current pulse which causes extremely rapid heating of the sample tube. One such heater circuit which can be employed in conjunction with this invention is a multi-stage capacitive discharge circuit such as is described in the parent of this application. Computer 22 controls operation of heater circuit 20 in accordance with a pre-specified operating sequence. Capillary tube 18 is connected to chromatography separation column 24 of conventional construction. Materials which elude from column 24 are sensed by flame ionization detector (FID) 26. As described previously, when components of the analyte pass through FID, charged species are formed which are detected by an electrometer.

A carrier gas such as hydrogen with the sample stream entrained on it enters the system at inlet 28. The pressure of the carrier gas and sample stream is continuously measured by monitor 30. Sample bulb 32 causes a small portion of the carrier gas and sample stream to be directed through chamber inlet conduit 34. A flow restrictor, which may be in the form of a short, small caliber piece of fused silica capillary tube 36 is provided so that the portion of the carrier gas and sample stream which is not flowing through chamber inlet conduit 34 is continually vented. The level of restriction imposed by restrictor 36 is selected to provide a desired flow rate into bulb 32.

In operation, the carrier gas and sample stream are directed through sample bulb 32 continuously. Thus sample is continuously delivered to chamber 12. Since cold nitrogen gas continually circulates through thermal focusing chamber 12, the sample stream entering becomes trapped in tube 18 through condensation. When injection onto column 24 is desired, a pulse of current is generated by circuit 20 thereby heating capillary tube 18 and causing the condensate to be vaporized and injected into column 24. Since heater circuit 20 resistively heats metal tube 18 in a few milliseconds, the sample is introduced as a very narrow sample plug into column 24 for separation. Upon completion of a heating cycle, the metal tube 18 begins to cool and within a few seconds, its temperature returns to a value sufficiently low to ensure complete collection of the sample. A series of high speed chromatagrams can be generated by consecutively alternating the heating and cooling cycles.

Since the sample vapor is delivered continuously to thermal modulation chamber 12 with the thermal modulation technique, "breakthrough" of sample vapor arriving at the chamber just after heating is inevitable (i.e. direct passage through the focusing chamber). As thermal focusing chamber 12 cools, the breakthrough gradually decreases until the trap temperature necessary for quantitative trapping is again achieved. For typical operation, the sample collection interval between injections is a few seconds and the injection bandwidth when sample tube 18 is heated is a few milliseconds. Thus the sample injected from sample tube 18 is enriched by about a factor of a thousand, and the detector signal from the breakthrough sample vapor may be insignificant.

After injection, current flow through metal capillary tube is stopped, causing it to cool and thus condense incoming sample components. The temperature of tube may, however, be adjusted to prevent certain highly volatile components of the mixture from being trapped. This is possible since higher initial temperatures for chamber 12 provide slower cooling rates and the more volatile components require significantly lower condensation temperatures.

Figure 2:
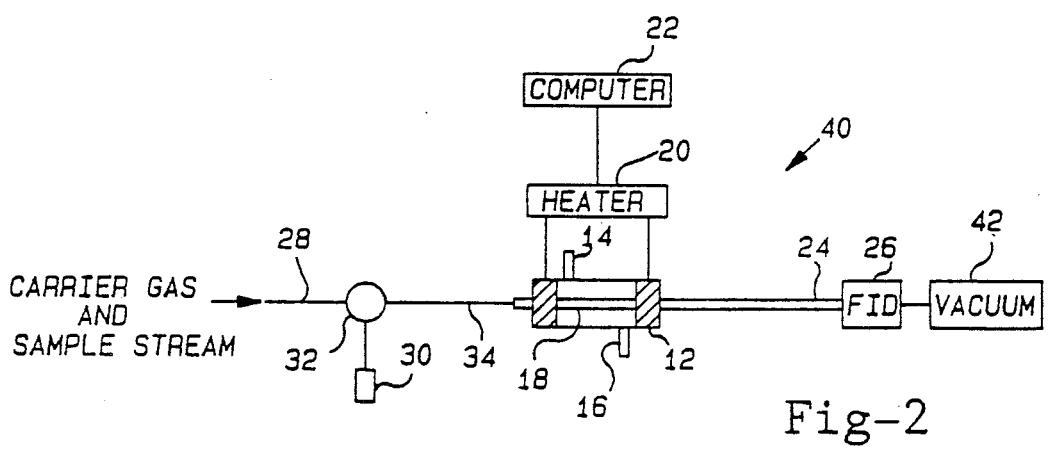
FIG. 2 is a schematic diagram of a gas chromatography system in accordance with a second embodiment of this invention intended for continuous ambient pressure sensing through use of a vacuum source at the column outlet.

FIG. 2 shows a second embodiment of a gas chromatography system in accordance with this invention which is generally designated by reference number 40. System 40 has many components which are identical to those of system 10 and are accordingly identified by like reference numbers. Gas chromatography system 40 differs from system 10 in that restrictor 36 is eliminated. Instead, a vacuum source 42 acts beyond detector 26, causing the system to draw sample at atmospheric pressure. For example, this system could be implemented as an air quality "sniffing" probe. Operation of system 40 proceeds like that of system 10 in that alternating heating and cooling cycles of the sample within thermal focusing chamber 12 occur, causing alternative trapping and injection of the components of the sample being evaluated.

Figure 3:
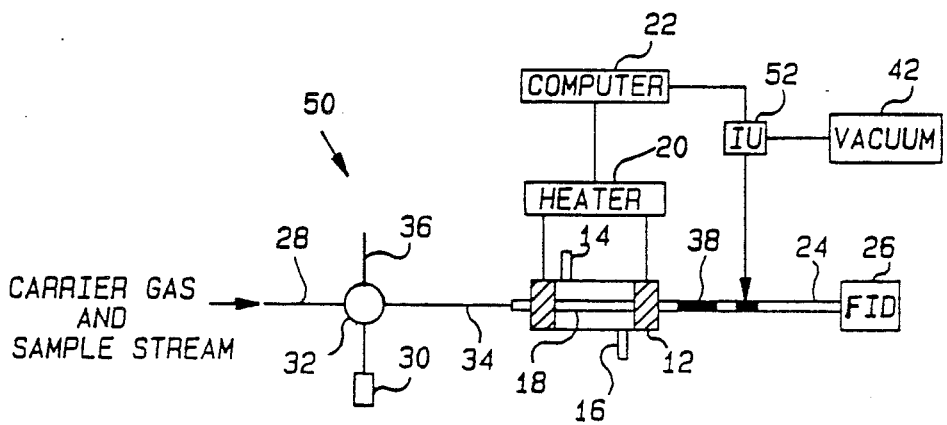
FIG. 3 is a schematic diagram of a gas chromatography system in accordance with a third embodiment of this invention providing a vacuum assisted backflush capability.

FIG. 3 illustrates gas chromatography system 50 according to a third embodiment of this invention. System 50 is generally consistent with that shown in FIG. 1, except that a vacuum backflush system in incorporated. Vacuum source 42 communicates with the inlet of column 24 and is controlled through interface unit 52 by computer 22. Interface unit 52 is preferably coupled to a pneumatically operated micro gas valve. As shown, system 50 is adapted to be used in conjunction with a carrier gas and sample stream supplied at a pressure above atmospheric which thus drives the carrier gas and sample stream through the system with the outlet of column 24 exposed to atmosphere. Vacuum source 42 is periodically connected with the inlet end of column 24 causing a reverse migration of components on the column. Restrictor 38 is provided to ensure reverse direction fluid flow through column 24. In some instances, high boiling point components which are contained in the sample and are not of interest, are admitted onto the column and would take an unacceptably long time to migrate down the entire column until elution at detector 26. Where high speed chromatagrams are desired, these slow moving high boiling point components would either compromise the sampling interval or give rise to distortion by appearing on successive chromatagrams. Accordingly, in the operation of gas chromatography system 50, following the separation step, vacuum source 42 communicates with the column to backflush the system. This process is preferably accomplished while thermal focusing chamber 12 is again at a low temperature, causing the next sample for injection to be simultaneously trapped while the backflush operation is occurring.

The inventors have conducted experiments of a prototype gas chromatography system. The system was based on a modified varian 3700 gas chromatography device. Sample tube 18 comprised a tube made of 70% Cu and 30% Ni, having a length of 25 cm and a 0.30 mm inside diameter. The experimental prototype column 24 comprised a 200 cm long, 0.25-mm i.d. fused silica capillary with a 0.1-micro m thick methyl silicone stationary phase (DB-5). The sample tube 18 was clamped between a pair of copper conductive blocks heated by 150 watt heating cartridges with Omega model CN9111J temperature controllers. Heater circuit 20 comprised a capacitive discharge system with 7 L-C sections, 2000 micro-F and 107 micro-H each, 0-80 V. The nitrogen gas passing through thermal focusing chamber 12 provided a −90° C. temperature. For the vacuum backflush system identified as chromatography system 50 in FIG. 3, the restrictor 38 comprised a 38-cm long, 0.1-mm i.d. deactivated fused silica capillary. The valves which were controlled through interface unit 52 was an SGE micro pneumatic on-off valve in "L" configuration with a 50 mm stem, and a Valco solenoid valve model H55P18DIA. Vacuum source 42 comprised a Cenco Hyvac 7, two-stage pump.

The experimental prototype was evaluated using a mixture containing n-heptane, toluene and p-xylene vapor in hydrogen carrier gas at concentrations of 13, 25 and 18 micro-L/L, respectively. For these experiments, metal sample tube 18 received a heating pulse every 10.4 seconds. The temperature of thermal focusing chamber 12 range from −95° C. just before the heating pulse to about 60° C. Backflush flow for system 50 was initiated 5.0 s after sample injection and was continued for 3.0 s.

While the above description constitutes the preferred embodiments of the present invention, it will be appreciated that the invention is susceptible of modification, variation and change without departing from the proper scope and fair meaning of the accompanying claims.

We claim:

1. A method of conducting gas chromatography procedures comprising the steps of:
   providing a source of a sample and a carrier gas,
   providing a thermal focusing chamber, with a sample tube passing therethrough for conducting said sample and said carrier gas,
   providing a chromatography separation column communicating with said sample tube,
   providing a detector for sensing the presence of components of said sample being eluded from said column,
   applying a pressure differential for causing said sample and said carrier gas to continuously flow into said sample tube, and
   modulating the temperature of said sample tube to cause at least some components of said sample to condense inside said sample tube and thereafter cause said condensed components to be injected into said column by increasing the temperature of said sample tube along with additional quantities of said sample continuously flowing through said sample tube.

2. A method of conducting gas chromatography procedures according to claim 1 wherein said step of applying a pressure differential comprises supplying said sample and carries gas at a positive gage pressure and venting said column to atmosphere.

3. A method of conducting gas chromatography procedures according to claim 1 wherein said step of applying a pressure differential comprises applying a vacuum to said column causing said sample at atmospheric pressure to be drawn into said sample tube and through said column.

4. A method of conducting gas chromatography according to claim 1 further comprising the step of periodically applying a vacuum to an entrance end of said column thereby backflushing said column.

5. A gas chromatography system comprising:
   a source of a sample,
   a source of a carrier gas,
   a thermal focusing chamber having means for cooling said chamber for condensing at least some components of said sample,
   a sample tube within said chamber for conducting said sample and said carrier gas through said chamber,
   inlet conduit means for providing a continuous supply of said sample and said carrier gas into said sample tube,
   temperature control means for rapidly increasing the temperature of said sample tube for vaporizing any of said sample components condensed within said sample tube,
   a chromatography separation column,
   control means for periodically causing said temperature control means to heat said sample tube thereby vaporizing said condensed sample components and injecting said condensed components into said column along with additional quantities of said sample continuously flowing through said sample tube, and
   detector means along said column for detecting the presence of components of said sample along said column.

6. A gas chromatography system according to claim 5 further comprising a restricted passage for allowing a portion of said sample and said carrier gas from said sources to escape while allowing a remaining portion to enter said sample tube.

7. A gas chromatography system according to claim 5 further comprising, a vacuum source communicating with an exit of said column for drawing said sample into said sample tube and through said column.

8. A gas chromatography system according to claim 5 further comprising a vacuum source communicating with an entrance end of said column for enabling backflushing of said column.

9. A gas chromatography system according to claim 5 wherein said means for cooling controls the temperature of said thermal focusing chamber to prevent at least some relatively highly volatile components of said sample from being condensed in said thermal focusing chamber.

* * * * *